United States Patent [19]
Jenner et al.

[11] Patent Number: 5,612,056
[45] Date of Patent: Mar. 18, 1997

[54] TRANSDERMAL FORMULATIONS

[75] Inventors: John Jenner; Dennis W. Swanston, both of Salisbury; Ahsan Saleem, Bootle, all of Great Britain

[73] Assignee: The Secretary of State for Defence in her Britannic Majesty's Government of the United Kingdom of Gt. Britain & Northern Ireland, England

[21] Appl. No.: 196,094

[22] PCT Filed: Aug. 21, 1992

[86] PCT No.: PCT/GB92/01547

§ 371 Date: Mar. 15, 1994

§ 102(e) Date: Mar. 15, 1994

[87] PCT Pub. No.: WO93/03767

PCT Pub. Date: Mar. 4, 1993

[30] Foreign Application Priority Data

Aug. 21, 1991 [GB] United Kingdom ............ 9118028

[51] Int. Cl.$^6$ ............................................. A61F 13/00
[52] U.S. Cl. ..................... 424/449; 424/448; 514/947
[58] Field of Search ..................... 424/448, 449; 514/947

[56] References Cited

U.S. PATENT DOCUMENTS

| | | | |
|---|---|---|---|
| 4,294,852 | 10/1981 | Wildnauer | 424/317 |
| 5,350,581 | 9/1994 | Kochinke | 424/443 |
| 5,352,457 | 10/1994 | Jenkins | 424/448 |
| 5,391,375 | 2/1995 | Hille | 424/449 |

FOREIGN PATENT DOCUMENTS

| | | |
|---|---|---|
| 0345081 | 6/1989 | European Pat. Off. . |
| 2163347 | 2/1986 | United Kingdom . |
| 9115176 | 10/1991 | WIPO . |

OTHER PUBLICATIONS

J. of Pharmaceutical Sciences/ 409 vol. 77, No. 5, May 1988 Kadir "Penetration of Adenosine into Excised Human Skin from Binary Vehicles: The Enhancement Factor".

Primary Examiner—D. Gabrielle Phelan
Attorney, Agent, or Firm—Nixon & Vanderhye

[57] ABSTRACT

An improved transdermal delivery composition is provided comprising a low molecular weight fatty acid, characterised in that it further comprises a long chain fatty acid or a long chain fatty acid lower alkyl ester, wherein the long chain is a $C_{13}$ to $C_{21}$ chain and preferably contains at least one cis-olefinic bond. Preferred long chain components are oleic acid and ethyl oleate while the preferred low molecular weight fatty acid is propionic acid. The compositions are particularly effective at transdermally delivering physostigmine and its analogues in a stable dosaged manner.

15 Claims, 4 Drawing Sheets

TRANSDERMAL FORMULATIONS

The present invention relates to prophylactic and therapeutic formulations having improved skin penetration efficacy, being particularly useful in the delivery of acetylcholinesterase (AchE) inhibitors of the carbamate base type, more particularly of the physostigmine type.

The carbamates pyridostigmine and physostigmine are non-competitive inhibitors of acetylcholinesterase but have the property of dissociating from that enzyme such that after a relatively short period, eg. about 15 minutes, significant reactivated esterase activity is achieved. This effect is in stark contrast to that of organophosphate nerve gents, such as sarin and tabun, which chemically alter the esterase active site, permanently destroying esterase activity and thus the cholinergic systems concerned.

It has been found that a prophylactic dose of such carbamates can be used to protect a proportion of a subject's acetylcholinesterase against interaction with organophosphates (OPs) by virtue of their ability to block the enzyme active site. While a treated subject may lose consiousness or suffer other symptoms when challenged with organophosphate it is found that the proportion of esterase protected by the physostigmine can be sufficient to prevent death, as and when it is released from blockade by the carbamate dissociating from it.

Obviously, for long term anticholinesterase protection or other long term reversable inhibition treatments a sustained release formulation would be required. An oral sustained release formulation would reduce the frequency of administration while providing a convenient dosage method which requires no special equipment. So far no satisfactory formulation has emerged to achieve this modest aim.

The carbamate in current use as a nerve agent prophylaxis is pyridostigmine and it is used in tablet form. Pyridostigmine does not cross the blood brain barrier and consequently provides no central nervous protection. The same chemical property which prevents pyridostigmine from entering the brain, its positive charge, will prevent it from penetrating the skin. Physostigmine however, carries no charge and is an ideal candidate for transdermal delivery. However physostigmine has a short plasma half life and a narrow therapeutic index which necessitates the use of a sustained release formulation.

While it is known to administer physostigmine by injection an attractive alternative route for administering protective doses is the transdermal route using a patch bearing a suitable transdermal delivery composition. A known such physostigmine delivery composition is disclosed by GB 2163347 A and comprises a 50% wt.:vol. mix of physostigmine with propionic acid. Recent work to find a treatment for Alzheimers disease (Christie et al; Br. J. Psychiatry, 138 46–50 (1981)) has identified such transdermal formulations which deliver physostigmine at therapeutically useful doses and a further recent study (Pardo et al; J. Pharm. Sci. 79 p573–578 (1990)) has shown that the thermodynamic activity of physostigmine, which drives the diffusion of drug into the skin, is highest from a binary vehicle of isopropyl myristate and isopropyl alcohol (9:1; vol./vol.).

These composition may be used to treat a variety of cholinergic nervous system disorders but when applied to the dosage requirements of organophosphate (OP) poisoning it is found that inconveniently large patch sizes are necessary. Furthermore, the large Mounts of physostigmine that must be provided on such patch may prove fatal should the wearer suffer a skin lesion, such as a penetrating wound, at the site of the patch.

The present invention provides improved compositions which enable increased amounts of basic compounds to be delivered transdermally per unit compound in the patch. Most beneficially the compositions are applied to delivery of basic compounds of non-ionic form, ie. those not committed to being ionised by way of, eg. quaternarised nitrogen groups. Thus use of the present compositions allows a reduction in the amount of compound required in a patch with the accompanying advantage that the area of the patch can be reduced.

It will be realised that the present compositions may be used to transdermally deliver basic (proton accepting) compounds, particularly physostigmine and its analogues, for any prophylactic or therapeutic purpose, particularly for long term treatments. Thus possible treatments of inter alia Alzheimer's disease, Parkinson's disease, Pick's disease, Gerstmann-Straussler Syndrome, Myasthenia Gravis and Glaucoma may be effected using such compositions. GB 2163347-A speculates further as to cholinergic disfunctions where such transdermal delivery might be used and these will also be potentially useful areas for application of the present compositions.

The particular preferred formulations of the invention not only achieve desired dosages but provide a stable suppression of enzyme activity.

In its broadest form, the present invention provides compositions comprising a low molecular weight fatty acid characterised in that they further comprise a long chain fatty acid or a long chain fatty acid lower alkyl ester, wherein the long chain is a $C_{13}$ to $C_{21}$ chain, preferably containing at least one cis-olefinic bond; and further it provides use of these compositions as transdermal delivery vehicles.

The preferred chain length for the long chain of the fatty acid or fatty acid ester, excluding the carboxyl group carbon, is $C_{15}$ to $C_{19}$, most preferably about $C_{17}$. Preferably the long chain is a straight (n—) chain and this preferably has only one cis-olefinic (C═C) bond. When the acid is lower alkyl esterified, the lower alkyl group preferably $C_1$ to $C_4$ alkyl, most preferably $C_1$ to $C_2$ alkyl. Thus myristeic acid is an example of a usable saturated acid, but longer unsaturated acids such as oleic acid are more preferred. The low molecular weight fatty acid component is preferably a $C_2$ to $C_4$ fatty acid, more preferably being propionic or butyric acid. A particularly preferred low molecular weight fatty acid component is propionic acid.

It will be realised by a man skilled in the art that increasing the length of the long chain fatty acid might cause increasing disruption of tissue lipid layers while decreasing the length might be expected to reduce the penetration of the composition, and thus the compound to be delivered which is contained within it, across the dermis; thus these factors, inter alia, will need to be considered when adapting the composition to a particular active ingredient. It will further be realised that the term active ingredient as used herein is that with primarily a prophylactic or therapeutic activity and not a particular activity associated with crossing the dermis.

Preferred ratios of the long chain fatty acid or its ester to the low molecular weight fatty acid are from 40:60 to 60:40 vol.:vol, more preferably 45:55 to 55:45 vol.:vol., most preferably about 50:50 vol.:vol. while the preferred content of the active ingredient in this mixture is from 10 to 50% wt./vol. of mixture. More preferably from 20 to 30% wt./vol. of mixture and most preferably about 25% wt./vol.

The transdermal delivery composition described above is particularly suited to the delivery of non-ionic basic anticholinesterase inhibiting compounds of the carbamate type, particularly physostigmine and its analogues. It will be realised that the composition will be useful for transdermal delivery of many other different types of basic, particularly non-ionic basic, compounds.

The preferred long chain fatty acid components oleic acid and ethyl oleate are toxicologically acceptable for drug administration but have never been used in a formulation of physostigmine for transdermal application. Neither oleic acid nor ethyl oleate affect the stability of physostigmine whereas the inventors' investigations with some long chain fatty acids and esters, eg. isopropyl myristate, have shown slow physostigmine deterioration. The use of an acidic component, in this case the low molecular weight fatty acid, eg. propionic acid, is required to solvate and neutralise basic active agent eg. physostigmine free base.

As stated above, carbamate prophylaxis of nerve agent poisoning depends upon a proportion of acetylcholinesterase (AchE) inhibited by a carbamate (eg. the physostigmine or pyridostigmine) being spared in the face of nerve agent poisoning, when all unbound AchE is phosphorylated by the OP nerve agent. After poisoning the carbamoylated portion of AchE is available for spontaneous reversal to functional enzyme restoring the body to normal physiological function. Thus the subject is either completely protected or at least saved from lethal effects of nerve agents. It is found that about 30% of the available AchE needs to be so protected to effect this prophylaxis.

The present inventors have studied physostigmine absorption through human skin to assess the feasibility of its transdermal delivery as a pretreatment for nerve agent poisoning. Penetration of radiolabelled physostigmine across human epidermis has been measured in vitro using glass diffusion cells wherein optimisation of physostigmine absorption was achieved by use of the present compositions as penetration enhancers.

The delivery of drugs by the transdermal route is an area of increasing interest and offers the advantage of allowing prolonged steady input of drug into the blood. However, the excellent barrier properties of the skin impose a major limitation on the drug with respect to required dosage. Consequently, prior to the development of a transdermal delivery system, it is necessary to determine whether the drug to be incorporated permeates human skin in the required therapeutic amount.

Clinical studies indicate that an intraveous infusion rate of 400 $\mu g.hr^{-1}$ produces blood cholinesterase inhibitions of approximately 30%. This inhibition does not cause overt signs of cholinesterase poisoning nor impair performance. When delivering a drug transdermally, if skin permeability becomes the limiting factor, bioavailability can be increased by using a larger surface area. Practical considerations limit the size of a patch for administration to humans to about 20 cm which would require a permeability rate of at least 20 $\mu g.cm^{-2}.hr^{-1}$ for feasible transdermal delivery of physostigmine. Higher permeability rates would allow the quantity of physostigmine and the patch size to be reduced, minimising the risk of physostigmine intoxication following injury at the patch site.

The suitability of the compositions of present invention for such transdermal delivery of active ingredients will now be illustrated by way of particular Examples of compositions of the present invention which are provided to aid a man skilled in the art to better comprehend their advantages. Other suitable compositions falling within the scope of the invention will occur to a skilled man in the light of these Examples.

Materials and methods: Chemicals

Figure 1:
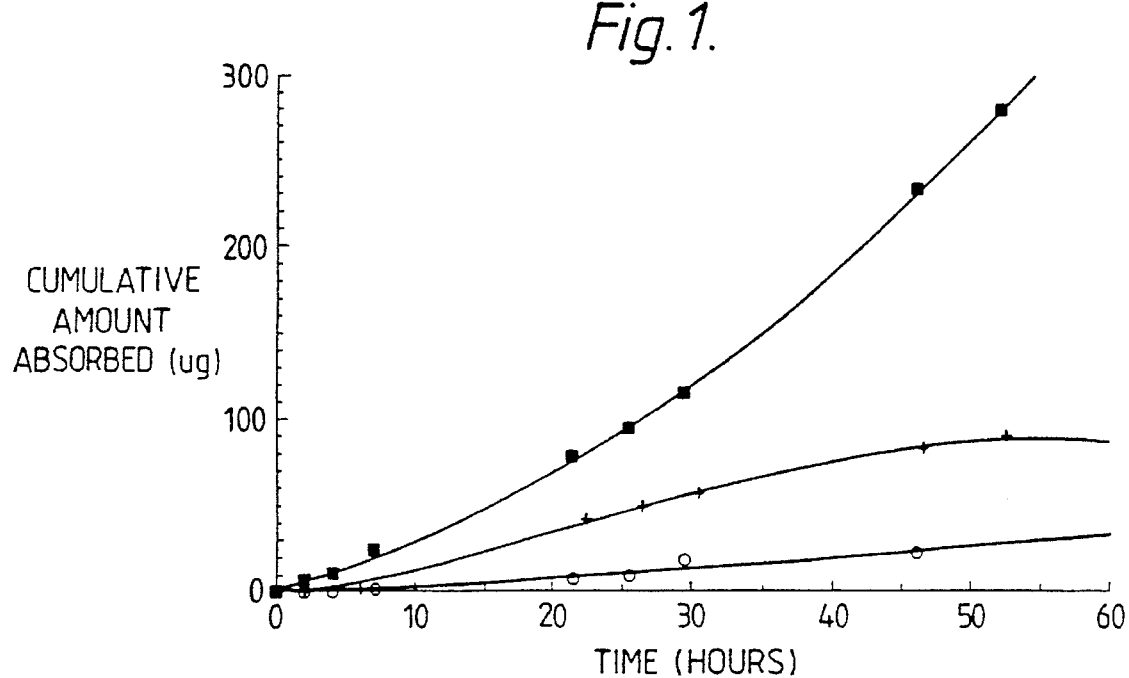
FIG. 1 Shows a graph of absorbed active compound (cumulative amount absorbed ($\mu$g)/time (hours) illustrating penetration of physostigmine across human epidermis from saturated (o) propylene glycol, (+) isopropyl myristate and (■) propylene glycol/oleic acid (10/90). Points are means of 3–5 runs.
Figure 2:
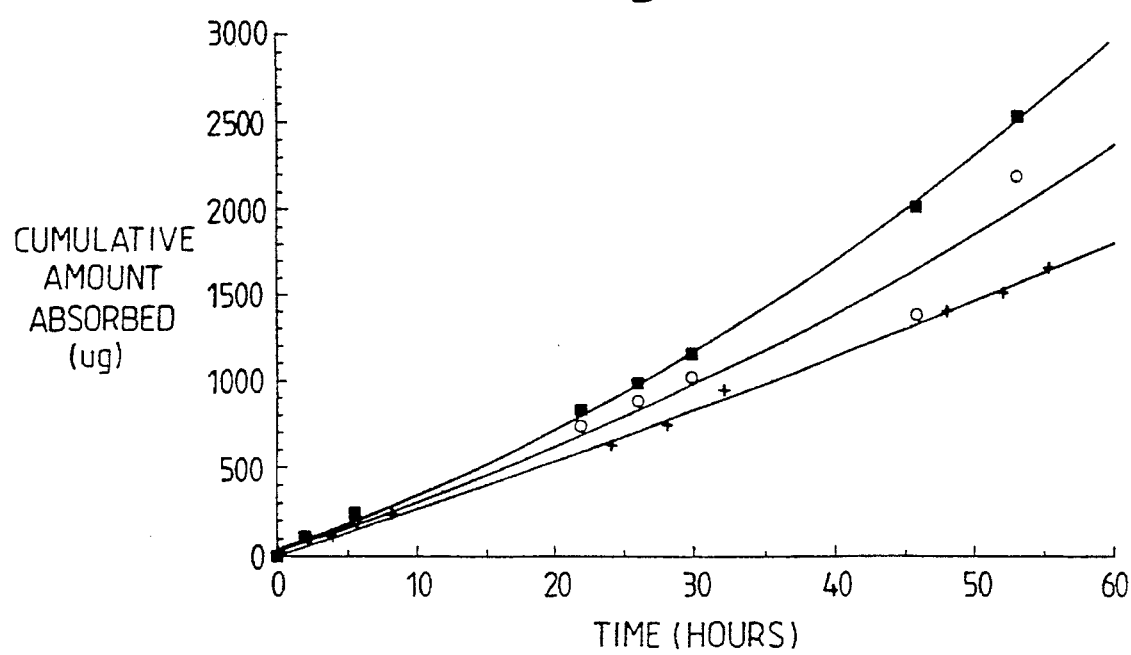
FIG. 2 Shows a graph of absorbed active compound (cumulative amount absorbed ($\mu$g)/time (hours) illustrating penetration of physostigmine across human epidermis from (+) 50% physostigmine in propionic acid. (o) 25% physostigmine in propionic acid/isopropyl myristate (50/50 vol/vol) and (■) 25% physostigmine in propionic acid/oleic acid (50/50 vol/vol). Points are means from 3–5 runs.
Figure 3:
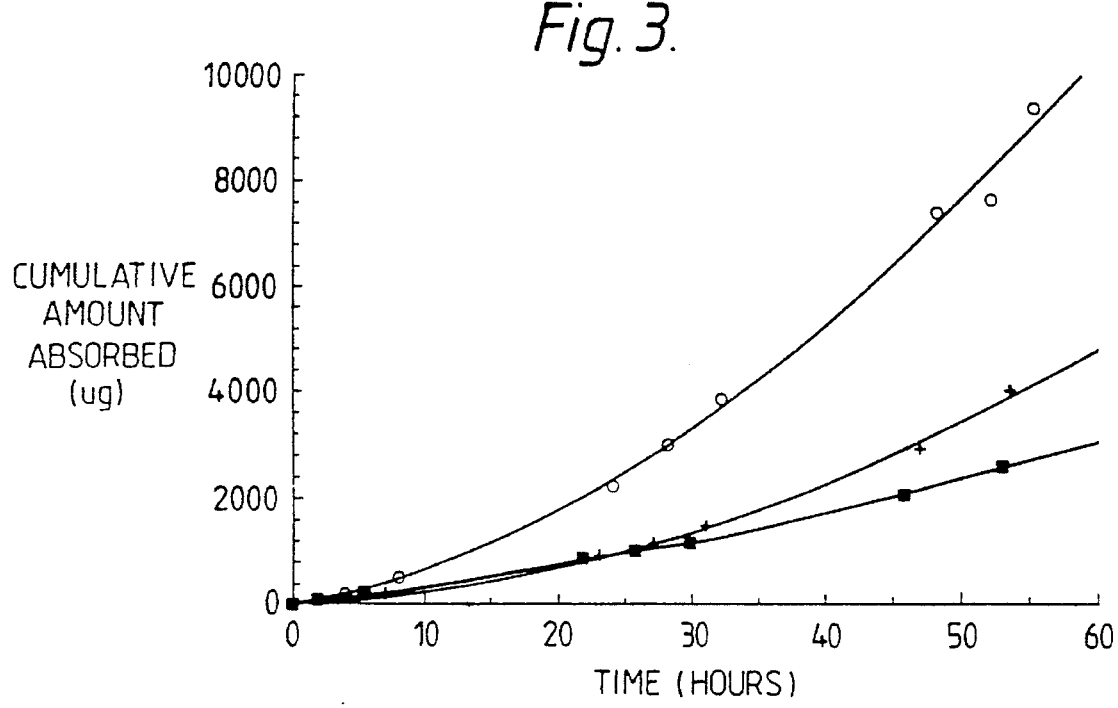
FIG. 3 Shows a graph of absorbed active compound (cumulative amount absorbed ($\mu$g)/time (hours) illustrating penetration of physostigmine across human epidermis from propionic acid/oleic acid (50/50 vol./vol.), (■) 1%; (+) 25%; and (o) 10% physostigmine (wt/vol.).
Figure 4:
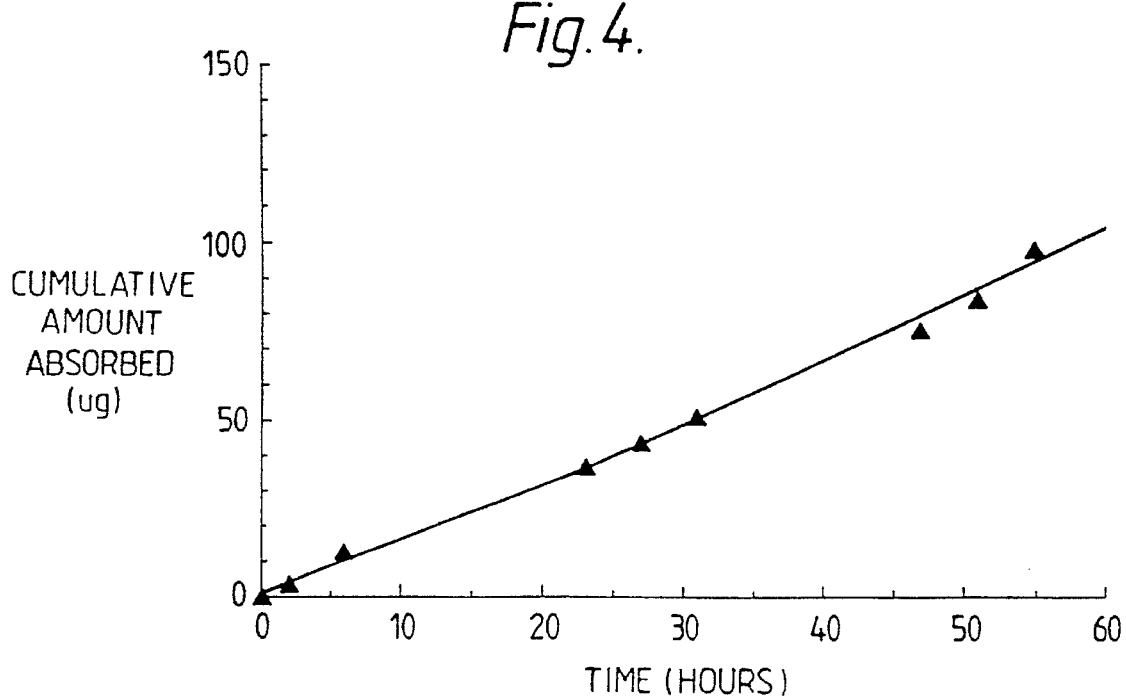
FIG. 4 Shows a graph of absorbed active compound (cumulative amount absorbed ($\mu$g)/time (hours) illustrating penetration of physostigmine across human epidermis from a 10% solution of propionic acid/oleic acid ( 10/90 vol./vol.).

[$^3$H] water and [$^3$H] physostigmine,>90% radiochemical purity were obtained from Amersham International plc (Amersham, UK). Ethyl oleate, squalene, propylene glycol, propionic acid (all>99%) and oleyl alcohol (66%) were obtained from Aldrich chemical company Ltd (Gillingham, UK). Isopropyl myristate (98%), N-hydroxyethyl lactamide (70% aqueous solution) and physostigmine (free base) were obtained from Sigma Chemical Company Ltd (Poole, ILK). Emulsifier-Safe scintillation fluid and Soluene-350 were obtained from United Technologies, Packard (Illinois, USA). Oleic acid (>99%) was obtained from BDH chemicals Ltd (Eastleigh, UK) and dipropylene glycol monomethyl ether was obtained from Dow Chemicals (Rotterdam).

Solubility studies

Between 10–20 mg of physostigmine base was weighed into a 1 ml volumetric flask. An initial 25 ml volume of the chosen vehicle was added to the flask and the mixture agitated ultrasonically for 30 minutes. If dissolution had not occurred at the end of this period, 10–50 $\mu$l further aliquots of vehicle were added and the process repeated until complete dissolution had occurred.

Partitioning Studies

A 2% physostigmine solution was prepared in the vehicle being evaluated. Two milliliters of this solution was placed in a vial and a known amount of radioactive physostigmine added (A0 cpm). The solution was shaken and a 50 μl aliquot taken for counting in 5 ml of scintillation fluid (A1 cpm). A weighed piece of human epidermis (W g) was placed in the vial containing the physostigmine solution and completely immersed. The vial was incubated for 48 hours at 30° C. with occasional shaking, a 50 μl aliquot taken and counted in 5 ml scintillation fluid (A2 cpm). 2 ml of physostigmine solution (2%) in each candidate vehicle were placed in individual test tubes and 10 μl of radioactive physostigmine stock added to each tube. A further 10 μl was added to 5 ml of scintillation fluid and counted to give a measure of the total radioactivity added (A0 cpm). Aliquots of each candidate solution were then counted to give measures of the total radioactivity in the solution after quenching (A1 cpm). The quench correction for each solution is given by:

$$\frac{A0}{A1}$$

A known weight of epidermis (Wg) was then added to each solution and equilibrated for 48 hrs at 30° C. with occasional shaking. The radioactivity remaining in each 2 ml of vehicle was then measured (A2 cpm) and the concentration of radioactivity in solution ($C_s$) calculated from:

$$C_s = \frac{A0}{A1} \cdot \frac{A2}{2} \text{ dpm/ml} \quad (1)$$

The epidermal membrane was blotted dry between sheets of filter paper, solubilised in 1 ml of Soluene-350 and counted in 10 ml of scintillation fluid (S1 cpm). Twenty five microliters of a standard physostigmine solution with a known amount of radioactivity (S0 cpm) was added to the vial which was recounted (S2 cpm). The concentration of radioactivity in the tissue, assuming the density of the skin to be 1 g/ml (Ct) was then calculated from:

$$C_t = \frac{S1 \cdot S0}{W(S2 - S1)} \text{ dpm/ml} \quad (2)$$

Background counts were also determined and corrected for from the tissue, soluene and scintillation fluid systems. The partition coefficient ($K_m$) was then calculated as follows:

$$K_m = \frac{\text{conc. in tissue}}{\text{conc. in solution}} = \frac{ct}{cs} \quad (3)$$

Preparation of Physostigmine Formulations

Saturated solutions of physostigmine in isopropyl myristate, propylene glycol and propylene glycol/oleic acid (50/50 vol./vol.) were prepared by adding an excess amount of physostigmine to 1 ml of the vehicle. The solutions were agitated using a vortex mixer and then allowed to stand. After five further mixings the excess physostigmine was allowed to settle. The solution, termed "saturated", was removed using a Pasteur pipette and then spiked with 5–10 μl of [$^3$H] physostigmine prior to use for percutaneous absorption studies.

All other formulations (wt./vol.) were prepared as follows. Physostigmine was weighed and transferred to a 10 ml round bottomed flask. The vehicle was pipetted into the flask and the sample spiked with 5–10 μl of [$^3$H] physostigmine. The mixture was then agitated in an ultrasonic bath until dissolution had occurred. All formulations were protected from light and stored at 4° C. until required.

Preparation of skin membranes

Human abdominal skin was obtained post mortem and stored in sealed polythene bags at −20° C. When required the tissue was allowed to thaw at room temperature and the subcutaneous fat removed. Epidermal sheets were separated from full-thickness skin by immersing in water at 60° C. for 45 seconds and gently peeling away the epidermis.

Diffusion Apparatus

Percutaneous absorption experiments were performed in vitro using glass diffusion cells. Epidermal membranes were mounted in Franz type diffusion cells having a cross-sectional area of 2.54 cm$^2$. The cells were housed in a water bath maintained at 30° C. and the upper surface of the membrane exposed to donor solution. The under surface of the membrane was bathed by 4–5 ml of continuously stirred receptor fluid.

Diffusion studies

Prior to application of the physostigmine formulation the integrity of each membrane preparation was assessed by determining the permeability to tritiated water. The water permeability experiments were run over a 6 hour period to ensure achievement of steady state conditions. Physiological saline was used as the receptor fluid and 1 ml of saline containing tritiated water (0.2 mCi. cm$^{-3}$) applied to the donor chamber. The receptor was then sampled (25 μl) at hourly intervals. At the end of the tritiated water run both donor and receptor solutions were removed and the skin surfaces rinsed 2–3 times with distilled water. The chambers were then filled with distilled water and left overnight to desorb any residual activity from the epidermal membranes.

The following day any membrane found having a permeability coefficient greater than 1.5×10$^{-3}$ cm hr$^{-1}$ was considered damaged and not used in subsequent permeability measurements. The receptor chambers filled with 50% aqueous ethanol and 200 μl of labelled physostigmine (1 μCi) applied to the donor chambers. The movement of physostigmine across the membrane was followed by sampling the receptor solution (50 μl) over a period of 3 days.

Receptor samples were counted in 5 ml of scintillation fluid using a 1215 Rackbeta II liquid scintillation counter.

Data Analysis.

Results from the absorption experiments were plotted as cumulative amount absorbed against time. The steady state penetration rate, or flux, J (μg.cm$^{-2}$.hr$^{-1}$), was calculated by linear regression analysis from the linear regions of the plots. The permeability coefficient, Kp (cm.hr$^{-1}$) was obtained from the expression $$J = \frac{Km \cdot D \cdot c}{s} = Kp\, c \quad (4)$$

Where c=penetrant concentration (μg cm$^{-3}$) in the donor chamber, Km=partition coefficient of the penetrant between the vehicle and the skin. D=diffusion coefficient of the penetrant in the epidermis and s=membrane thickness.

The intercept on the time axis is termed the lag time (τ) and is related to the diffusion coefficient, D by $$(\tau) = \frac{s^2}{6D} \quad (5)$$

The flux can also be written in terms of the activity of the drug in the vehicle (a)

$$J = \frac{a\, D}{f s} \quad (6)$$

where f is the activity coefficient of the drug in the skin barrier, f is usually taken to be constant, so changes in penetration are attributed to alterations in the activity of the drug in the vehicle. By definition a solid has a thermodynamic activity of unity, therefore a saturated solution which is in equilibrium with the solid must also have an activity of unity. Therefore under ideal conditions the maximum penetration rate will be achieved from saturated solutions of the drug. Activity measurements are difficult to make and usually the ratio of concentration of solute to its solubility (percent saturation) value is determined to give an indication of the activity or "leaving tendency" of the penetrant in the vehicle. In practice the amount of drug in the donor solution will deplete during an experiment but if the depletion does not exceed 10% of the total amount in the donor the effect on penetration rate will be negligible. If the drug in the donor solution is reduced by less than 10% during an experiment the donor is assumed to be a non-depleting source and the experiment is carried out under infinite dose conditions.

Damage Ratios.

Water permeability damage ratios were determined to assess the membrane damaging potential of the various physostigmine formulations. This involved the measurement of the permeability coefficient of tritiated water through the membrane before and after application of the test formulation to the epidermal surface for a given period of time. The damage ratio (DR) was then given by $$DR = \frac{\text{water } Kp \text{ after vehicle application}}{\text{water } Kp \text{ before vehicle application}} \quad (6)$$

EXPERIMENTATION

Propylene glycol, isopropyl myristate, and propylene glycol/oleic acid (50/50 vol./vol.) were selected as comparative compositions for evaluation as vehicles for transdermal physostigmine delivery. Formulations of physostigmine in two component systems consisting of propionic acid/isopropyl myristate (50/50 vol./vol.) and propionic acid/oleic acid (50/50 vol./vol.) were evaluated against a patent formulation of 50% physostigmine in propionic acid (as per GB 2163347A). The effects of changing the concentration of physostigmine and the vehicle ratios of the propionic acid/oleic acid were also investigated.

Partitioning and solubility studies were used to evaluate oleyl alcohol, ethyl oleate, squalene, dipropylene glycol monomethyl ether, and N-hydroxyethyl lactamide as alternative vehicles for transdermal physostigmine delivery.

RESULTS

The time-course profiles for physostigmine penetration across human epidermis from the formulations investigated are presented in FIGS. 1–4. The corresponding permeability data is summarised in Table 1. Apart from the saturated isopropyl myristate and the 1% and 10% propionic acid/oleic acid formulations, penetration was less than 10% of applied dose which satisfies infinite dose conditions (ie. a non-depleting donor source) ensuring achievement and maintenance of steady-state conditions. Physostigmine rapidly depleted from the isopropyl myristate formulation (FIG. 1). As a result only a transient steady state was observed with almost 50% of applied dose being absorbed by 50 hrs.

Physostigmine must be chemically stable in each formulation during the period of diffusion measurement. Physostigmine breaks down to rubreserine and other degradation products by hydrolysis and subsequent oxidation, promoted by light and heat. Rubreserine is bright red and of the formulations investigated in this study only the propylene glycol, propylene glycol/oleic acid and N-hydroxyethyl lactamide acquired a pink/red colouration (over 10–24 hours). The precise extent of this breakdown was not determined. The solutions, termed "saturated", of isopropyl myristate, propylene glycol, and propylene glycol/oleic acid used to obtain flux rates shown in Table 1 were prepared by vortex mixing as outlined in materials and methods. Subsequent analysis by UV spectroscopy and comparison to solutions prepared by sonication showed them to have the saturations shown in Table 1. The discrepancy was probably due to inadequate agitation from vortex mixing as opposed to sonication. Diffusion rates from these vehicles are too low to allow the use of a practical patch size but it is unlikely that chemical instability or the discrepancy in saturation is responsible for this. The difference in diffusion rates between these vehicles and those containing propionic acid is too large to be overcome by increasing the concentration to saturation.

Use of propionic acid as a co-solvent with isopropyl myristate and oleic acid increased the solubility and stability of physostigmine (FIG. 2). The two component based physostigmine formulations, 25% in propionic acid/isopropyl myristate and 25% in propionic acid/oleic acid achieved higher transdermal fluxes (17 $\mu g.cm^{-2}.hr^{-1}$ and 24 $\mu g.cm^{-2}.hr^{-1}$ respectively) than the 50% propionic acid formulation (13 $\mu g.cm^{-2}hr^{-1}$; Table 1). Use of saturated solutions of physostigmine may increase fluxes from the two-component systems and it may be concluded that both the two-component systems are capable of delivering therapeutic amounts of physostigmine via the skin from patches with the areas shown in Table 2.

The increased fluxes observed from the two-component systems appear to be due to a combination of partitioning and diffusivity effects. These vehicles have similar partition coefficients, $K_m$, (Table 3) allowing favourable partitioning of physostigmine into the skin. It has been postulated that oleic acid and isopropyl myristate enhance penetration by interfering with the lipid layers of the stratum corneum and opening pathways for diffusion (Albery et al, J. Pharm. Pharmacol. 31 140–147 (1979)). This mechanism entails diffusion of the enhancer into the stratum corneum before enhancement is seen, which may account for the longer lag times from these vehicles.

Decreasing the physostigmine concentration in the propionic acid/oleic acid vehicle resulted in large increases in skin permeability (FIG. 3). These increases were however associated with increased water damage ratios (DR), as shown in Table 4, indicating membrane damage was responsible for the increased permeability from the 1% and 10% formulations as compared to oleic acid (DR=1.5). The DR of caused by the 25% formulation represents little damage to the barrier layer. Though propionic acid is irritant, physostigmine in propionic acid is likely to form the propionate and thus reduce or eliminate irritancy in formulations containing high concentrations of physostigmine. At lower concentrations there may be sufficient free acid in the formulation to cause membrane damage.

To produce a non-damaging formulation containing 10% physostigmine the ratio of propionic acid to oleic acid was reduced from 50/50 to 10/90 (FIG. 4). This vehicle was saturated with physostigmine and would have been expected to have been non-irritant. Oleic acid still appeared to interact with the skin lipid as indicated by the long lag time, but the transdermal flux of physostigmine was very low. This may be due to the less favourable partition coefficient of physostigmine from oleic acid than from 50/50 propionic acid/oleic acid. Increasing the content of oleic acid might therefore decrease the partitioning of physostigmine into the epidermis.

Concentration and partitioning are critical determinants of transdermal flux as shown by the steady state flux relationship (Eqn 4). It follows that increases in $K_m$ and C will lead to higher flux rates. However, these two parameters are interdependent in that a vehicle with a high solubility for physostigmine will be less likely to allow physostigmine partitioning into skin and vice versa. As predicted squalene, isopropyl myristate and ethyl oleate all have relatively low solubilities for physostigmine but high Km values (Table 3). Conversely oleyl alcohol, dipropylene glycol monomethyl ether, N-hydroxyethyl lactamide and oleic acid have greater solubility for physostigmine but lower $K_m$ values. It is apparent that a compromise has to be sought between $K_m$ and c when optimising vehicle formulations and this has been achieved with the two-component systems tested to date. Of the five preferred alternative vehicles under evaluation, ethyl oleate in combination with propionic acid appears to be the best vehicle for transdermal physostigmine delivery. It has a more favourable $K_m$ than oleic acid and contains the cis double bond which is thought to be responsible for the enhancing effects of that compound.

While isopropyl myristate enhances percutaneous absorption by increasing the partitioning of physostigmine into skin, oleic acid and ethyl oleate increase both the partitioning and diffusivity through this tissue. Furthermore isopropyl myristate is found to affect physostigmine stability, use of the isopropyl myristate containing compositions of the invention leading to a very slow production of a pink colouration indicative of break down products. Inclusion of oleic acid and ethyl oleate in transdermal formulations allows the use of a smaller transdermal patch for human dosaging (for example ca. 16–20 cm$^2$:) containing less physostigmine for a given dosage requirement thus reducing the risk of poisoning from mechanical damage to the patch and underlying skin.

TABLE 1

Transdermal fluxes (J) and lagtimes ($\tau$) for physostigmine penetration through human epidermis.

| VEHICLE | Conc. Physo % w/v | % SAT * | J µg cm$^2$ hr$^{-1}$ | lagtime (Y) hrs |
|---|---|---|---|---|
| Isopropyl Myristate | 0.2 | 17 | 0.71 ± 0.22 (4) | 7 |
| Propylene Glycol | 2.0 | 26 | 0.21 ± 0.07 (5) | 7 |
| Propylene Glycol/Oleic Acid ** | 2.7 | 54 | 2.83 ± 0.70 (3) | 14 |
| Propionic Acid | 50 | 100 | 13.0 ± 3.93 (4) | 5 |
| Proponic Acid/Isopropyl Myristate** (Example 1) | 25 | 83 | 17.1 ± 6.22 (3) | 8 |
| Propionic Acid/Oleic Acid ** (Example 2) | 25 | 67 | 24.1 ± 9.48 (4) | 11 |
| Propionic Acid/Oleic Acid ** (Example 3) | 10 | 22 | 91.8 ± 8.98 (3) | — |
| Propionic Acid/Oleic Acid ** (Example 4) | 1 | 2 | 39.8 ± 7.5 | — |
| Propionic Acid/Oleic Acid (10/90) (Example 5) | 10 | 100 | 0.83 ± 0.06 | 11 |

( ) = mean number of determinations
* = % saturations using solubilities shown in Table 3
** = 50/50 vol./vol.
(10/90) = 10/90 vol./vol.
Note:
Ethyl oleate/propionic acid (50/50 vol./vol.) gives J = 19.1 ± 7.1

TABLE 2

Estimated patch sizes required to deliver a prophylactic dose of physostigmine.

| FORMULATION | | PATCH SIZE cm$^2$ |
|---|---|---|
| Propionic Acid 50% physostigmine (w/v) | | 30 |
| Propionic Acid/Isopropyl Myristate (50/50 vol/vol) 25% physostigmine (w/v) | | 23 |
| Propionic Acid/ Oleic Acid (50/50 vol/vol) 25% physostigmine (w/v) | (Example 1) | 16 |

TABLE 3

Solubility and partitioning data for physostigmine.

| VEHICLE | SOLUBILITY IN VEHICLE g cm$^3$ | PARTITION COEFFICIENT (VEHICLE:SKIN) ($K_m$) |
|---|---|---|
| Squalene | <10 | 45 |
| Isopropyl Myristate | 120 | 11 |
| Propionic Acid/Isopropyl Myristate(50/50) Example 1 | 17 | 10 |
| Propionic Acid/Oleic Acid (50/50) Example 2 | 400 | 1.6 |
| Oleyl Alcohol | 500 | 1.2 |
| Dipropylene Glycol Monomethyl Ether | 60 | 0.6 |
| Oleic Acid | 250 | 0.5 |
| N-hydroxyethyl Lactimide | 67 | 0.3 |
| Propylene glycol | 77 | — |
| Propylene glycol/Oleic Acid (50/50) | 50 | — |
| Propionic Acid/Oleic Acid (10/90)Example 5 | 80 | — |

Solubilities determined by sonication as described in materials and methods. All proportions are vol/vol (eg (10/90)).

TABLE 4

Damaging Potential of propionic/oleic acid (50/50 vol./vol.).

| VEHICLE | DAMAGE RATIO |
|---|---|
| Propionic Acid/Oleic Acid (50/50) 25% physostigmine (w/v) Example 2 | 2.4 ± 0.2 |
| Propionic Acid/Oleic Acid (50/50) 10% physostigmine (w/v) Example 3 | 8.2 ± 1.2 |
| Propionic Acid/Oleic Acid (50/50) 1% physostigmine (w/v) Example 4 | 10.6 ± 2.3 |

* DR values for oleic acid = 1.4 ± 0.2 (3)
Damage ratio - Ratio of tritiated water permeability constants before and after exposure to formulation as detailed in materials and methods.

To further investigate the efficacy of the compositions of the present invention the use of propionic acid and oleic acid as vehicles for the transdermal delivery of physostigmine to the guinea pig has been investigated. These experiments show that formulations of the invention containing oleic acid are non-irritant after a 48 hour application.

MATERIALS AND METHODS

Materials chemicals Physostigmine (Sigma Chemical company, Poole, Dorset), propionic acid (Aldrich, Gillingham, Dorset) and oleic acid (British Drug Houses, Poole, Dorset) were supplied >99% pure and used as supplied.

Methods

Animals Guinea pigs (Dunkin-Hartley) were purchased from Interfauna ltd, kept in the Experimental Animal House throughout the experiments and allowed access to food and water ad libitum. For experiments measuring cholinesterase activity female guinea pigs (700–1200 g) were used and for the irritancy studies male animals (300–500 g) were used.

Physostigmine formulations. Physostigmine in propionic acid was prepared by dissolving physostigmine free base in propionic acid in equal proportions (wt./vol.) with sonication. Oleic acid was included in the mixture by dissolving 25% (wt./vol.) physostigmine free base in a 50:50 (vol./vol.) mixture of propionic and oleic acids.

Figure 5:
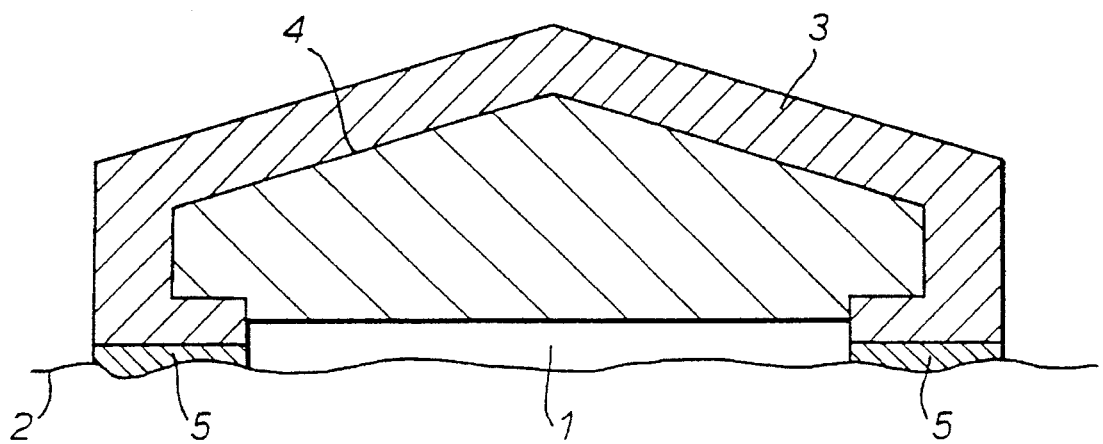
FIG. 5 Shows a diagrammatic cross section through a transdermal applicator used to apply physostigmine to guinea-pig skin; the applicator being glued to an area of close clipped skin on the dorsal thoracic area approximately 2 cm caudal of the ears.

Application of formulations. Formulations (1) were applied to a close clipped area of skin (2) in a rubber cap (3) taken from the plunger of a disposable syringe and referred to as the "applicator". The dead space of the applicator was filled with silicon rubber (4) to leave a volume of approximately 100 µl which was filled with candidate formulation (FIG. 5). The cup was glued with adhesive (5) to an area of preclipped skin of the dorsal thoracic region approximately 2 cm caudal of the ears, with cyanoacrylate adhesive. SuperGlue Xtra (RTM) formulated as a gel was found to be the most effective because it filled the area around the hair stubble and produced a more effective seal than liquid adhesives.

Applicators containing physostigmine were applied after blood sampling on the first day and removed after blood sampling on the third day of the experiment. Animals were lightly anaesthetised with Halothane to facilitate removal of the applicators, which could be pulled off by hand, and the application site was cleaned with aqueous alcohol to remove any remaining medicament. The area of application was 1 cm$^2$ for the physostigmine in propionic acid and 0.5 cm$^2$ for the physostigmine in propionic and oleic acid mixture.

Blood sampling and assay of cholinesterase. Blood was sampled by venepuncture of the ear vein, daily for five days and again on the seventh day, directly into sample tubes containing EDTA anticoagulant. Blood samples were kept on ice until assayed. Red blood cells (rbc) were separated by centrifugation (30 secs at 14,000 rpm in an Eppendorf 5415 centrifuge), plasma was reserved and the rbc's washed in ice cold saline. Washed cells were resuspended to original volume in ice cold saline. Haematocrits of the original blood and resuspended cells were measured using the Hawksley microhaematocrit system.

Aceytlcholinesterase activity was assayed by the method of Ellman et al; Biochem. Parmacol. 7 88—(1961). Assay mixtures contained either rbc or plasma (diluted 1:600 in final assay mixture), 0.01M 5,5'-dithiobis-2-nitrobenzoic acid (DTNB) and 1 mM acetylthiocholine in 0.1M phosphate buffer. Assay volumes were made up to a final volume of 5 ml and divided between two cuvettes for spectrophotometric monitoring (Pye-Unicam SP 8–100). The reaction was followed at 412 nm for 10 minutes (uninhibited) or 20 minutes (inhibited) and the initial reaction rate calculated from graphs of absorbance change against time. The assay was calibrated daily with cysteine standard solutions. Reactions were started by addition of substrate.

Blanks used in the spectrophotometer reference cells contained all reaction constituents except substrate. Spontaneous hydrolysis rates were measured separately and subtracted from enzyme catalysed rates. Corrections were made using haematocrit values so that enzyme activities could be expressed as amount product.min$^{-1}$.ml$^{-1}$ original blood volume.

Enzyme activities on day one were used as baseline values for each individual and result expressed as percent inhibition of this value. A control group were bled each day for a week without treatment with physostigmine to show any effects of repeat bleeding.

Irritancy studies. Preclipped male guinea pigs (300–500 g) were exposed percutaneously to the oleic acid formulation (25 µl) for 48 hours with the application site occluded. The site was washed with alcohol and water to remove any excess formulation and the application sites scored using a Draize Scoring system. Scores were averaged as outlined by the EEC Guideline No L/257: Off. J. Eur. Community 26 19 (1983).

RESULTS

Figure 6:
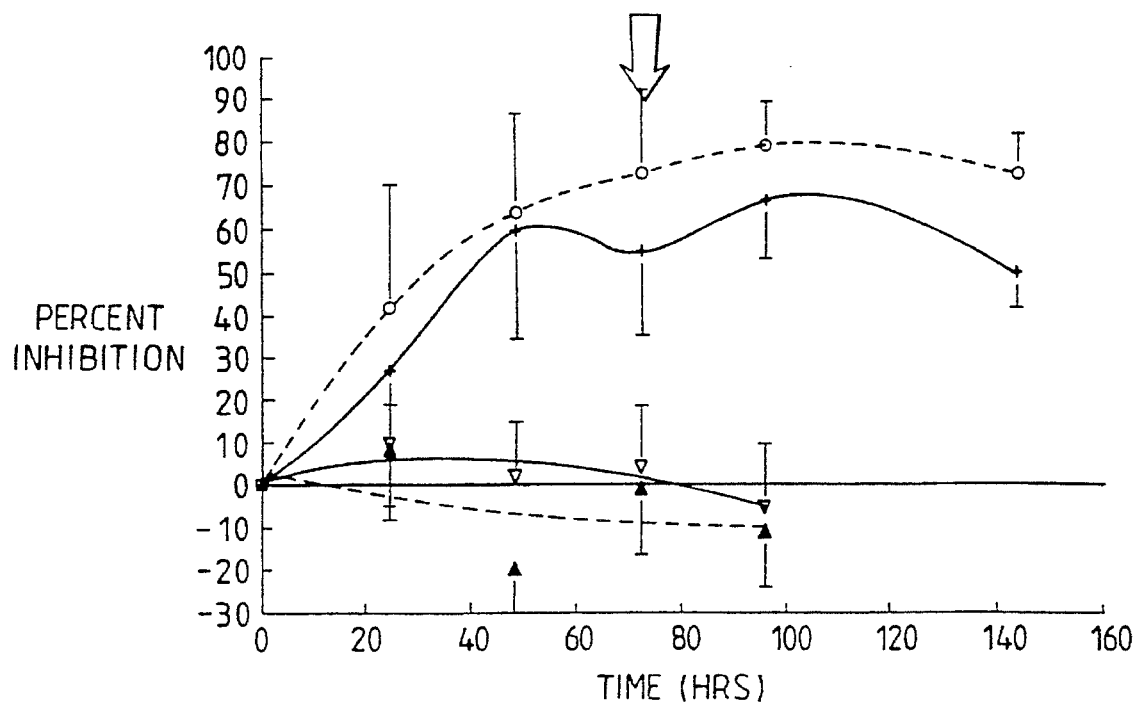
FIG. 6 Shows a graph of blood cholinesterase inhibition by transdermal physostigmine in propionic acid (50:50; wt./vol.) with the applicator being applied at time zero and removed at 72 hrs (arrowed). Plasma cholinesterase activities are shown by broken lines, red cell activities by solid lines and triangles denote untreated controls. Points are means of +/− SD of 5 animals. Application area is 1 $cm^2$.

Physostigmine in propionic acid (50:50; wt./vol.) produced an increasing inhibition of plasma and red cell cholinesterases until the removal of the transdermal applicator after 72 hrs (FIG. 6). The inhibition continued to increase over the following 24 hrs. Activities had started to recover 72 hrs after applicator removal but plasma and rbc cholinesterases were still inhibited by greater than 50% at this time. One animal in this group died within 24 hrs of treatment, all other animals showed no signs of cholinesterase poisoning ("sign free").

Figure 7:
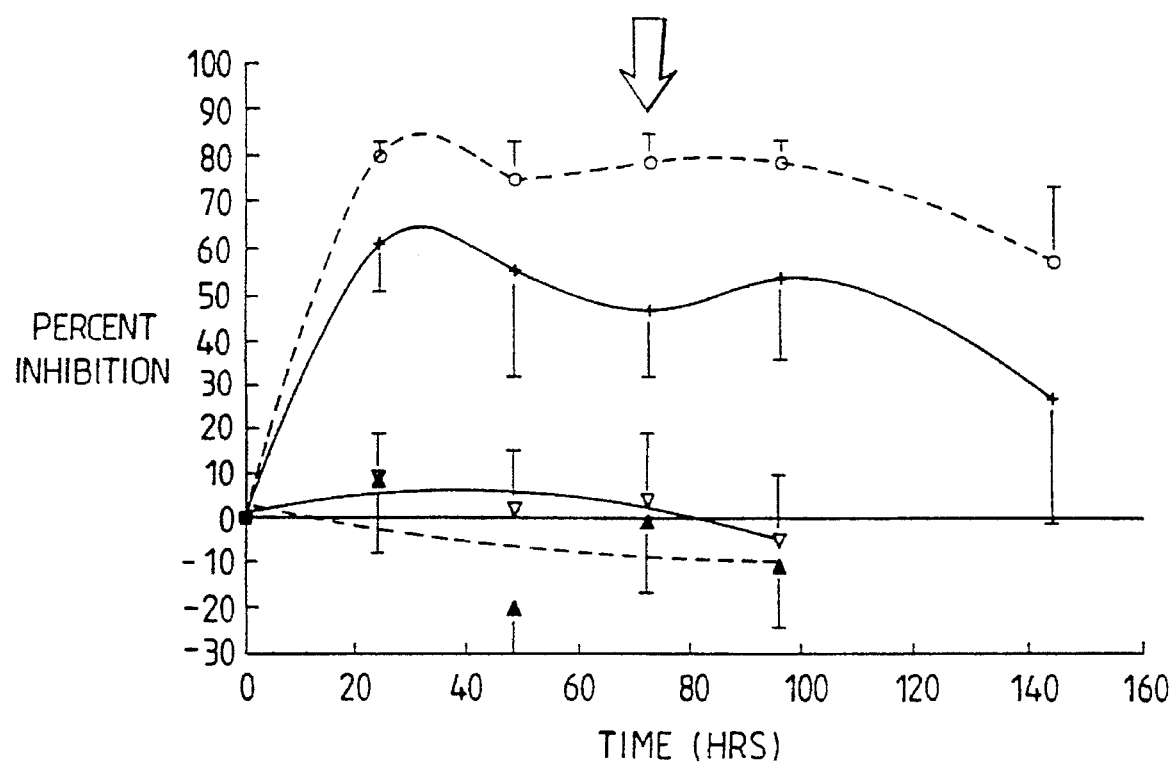
FIG. 7 Shows a graph of inhibition of blood cholinesterase by 25% wt./vol. physostigmine in propionic/oleic acid mixture (50:50; vol./vol.). The applicator was applied at time zero and removed after 72 hrs (arrowed). Plasma cholinesterase activities are shown by broken lines, red cell activities by solid lines and triangles denote untreated controls. Paints are means of +/− SD of 5 animals. Application area is 0.5 $cm^2$.

Physostigmine (25%; w/v) in propionic and oleic acids (50:50; v/v) produced 80% inhibition of plasma cholinesterase and 60% inhibition of rbc cholinesterase after 24 hrs (FIG. 7). These inhibitions were maintained until 24 hrs after applicator removal. Seventy two hours after removal of the applicator inhibitions had fallen to 60% (plasma) and 30% (rbc). Two of the animals in this group died within 24 hrs of application, the remainder were "sign free" for the duration of the experiment.

The 25% (w/v) physostigmine in propionic and oleic acids (50:50; v/v) was found to be non-irritant in the modified Draize test. Of the six animals treated 3 showed mild erythema 24 hrs after application and 2 at 48 hrs. Six and seven days after treatment 5 of the 6 animals showed mild diffuse scaling of the application site (Table 5). The average scores for erythema, oedema or desquamation did not exceed 2 at any time.

In this study physostigmine could be delivered by the transdermal route to guinea pigs in quantities sufficient to inhibit blood cholinesterases. Moreover inclusion of oleic acid in the formulation reduced the concentration of physostigmine and the area of the application required to produce blood cholinesterase inhibition (approximately 80% in plasma, 60% in rbc).

It was not possible to reproduce the results of GB 2163347A where a constant 30% inhibition of guinea pig whole blood cholinesterase was achieved from the physostigmine in propionic acid formulation between 5 hrs and 3 days from a 1 cm$^2$ area; a constant level of inhibition was not produced from this formulation.

Physostigmine is labile in guinea pig blood with a plasma half life of approximately 40–50 minutes (Lukey et al; J. Pharm. Sci. 79 796–798. This rapid elimination of active physostigmine means that persistence of blood cholinesterase inhibition for 3 days after cessation of treatment indicates continued delivery of physostigmine into the blood from a depot. This depot effect could be clinically beneficial or disadvantageous depending upon circumstance. Loading the depot by short term patch application would reduce the risk of irritancy or sensitisation from repeated treatments. Conversely the presence of a loaded depot would maintain dosing after removal of the patch which might be undesirable if the patient became a casualty and required drug treatment.

The location of the depot is open to conjecture, since depot effects are not seen when physostigmine is given intravenously the depot is probably in the skin. The stratum corneum is the most likely site. Drug which partitioned into this layer will slowly diffuse into the blood. However, the possibility that the depot resides elsewhere, for instance in the upper layers of the dermis, cannot be excluded on current data.

Inhibitions of blood cholinesterase in this study are higher than required to protect against nerve agent poisoning (30%). Deaths in the early part of the treatment period were associated with animals which had succeeded in scratching medicament out of the applicator. It is probable that these animals ingested a bolus dose of physostigmine which, combined with the transdermal dose, proved fatal. The area of application is thus required to be tailored to the particular recipient to achieve the desired inhibition as will be realised by the skilled man.

The inclusion of oleic acid, ethyl oleate or isopropyl myristate allowed both the amount of physostigmine in the formulation and the patch size, to be halved. This accords with the in vitro observations that oleic acid doubled the rate of percutaneous penetration.

To be clinically useful, a transdermal preparation of physostigmine must be non-irritant. Though propionic acid alone is irritant to the skin, a 50:50 mixture with physostigmine is non-irritant (GB 2163347A). In the present studies a 48 hr contact time with a formulation containing oleic acid produced very mild erythema and scaling with average scores of less than 2, which do not classify the formulation as irritant under EEC guideline L/257.

Addition of oleic acid to the mixture allowed the application area to be reduced by half (0.5 cm$^2$) and the content of physostigmine to be reduced to 25% whilst producing similar inhibitions of blood cholinesterases but reaching a constant inhibition before 24 hrs. The efficiency of these formulations in delivering physostigmine transdermally, particularly the oleic acid and ethyl oleate compositions, indicates the possibility of further reducing the patch size in order to attain the 30% inhibition of cholinesterase. Both formulations produce inhibitions of blood cholinesterases which persist for 72 hrs after removal of physostigmine from the skin. Inclusion of oleic acid in the formulation does not produce an irritant response in guinea pigs after 48 hr application.

TABLE 5

| Time after application | Average scores (Draize) | | |
|---|---|---|---|
| (days) | Erythema | Oedema | Desquamation |
| 1 | 0.5 | 0 | 0 |
| 2 | 0.33 | 0 | 0 |
| 3 | 0 | 0 | 0 |
| 6 | 0 | 0 | 0.9 |
| 7 | 0 | 0 | 0.9 |

TABLE 5-continued

Primary irritancy of physostigmine (25%;wt/vol) in propionic and oleic acids (50:50 vol/vol). Average Draize scores are shown for a group of six animals against time after the first application. An average score of two is required to classify a compound as irritant.

Example of liquid filled transdermal patch comprising a formulation of the invention.

A liquid filled transdermal patch comprising a composition according to Example 2 was assembled using tapes and permeable membranes supplied by 3M-Medica. The diffusion of physostigmine through calliper membranes containing various concentrations of vinyl acetate was measured using Franz type diffusion cells. A membrane containing 19% vinyl acetate (MSP 987192) allowed diffusion of physostigmine at a rate greater than that across isolated epidermis. This membrane was used to make a liquid filled patch with an impermeable backing (Scotchpak 1006-RTM) and was stuck to the skin using silicon based pressure sensitive adhesive (Dow-Corning 282A).

We claim:

1. A topical composition for transdermal application comprising:

(a) a $C_2$ to $C_4$ fatty acid, (b) oleic acid or a $C_1$ to $C_4$ alkyl ester thereof in a ratio of (b) to (a) of 40:60 to 60:40 vol./vol., and (c) 10–50% wt./vol of a therapeutic and/or prophylactic agent comprising a carbamate acetylcholinesterase inhibiting compound.

2. A composition as claimed in claim 1 wherein the carbamate acetylcholinesterase inhibiting compound is physostigmine.

3. A composition as claimed in claim 1 wherein component (b) is ethyl oleate.

4. A composition as claimed in claim 1 wherein the ratio of the oleic acid or its ester (b) to the fatty acid (a) is from 45:55 to 55:45 vol/vol.

5. A composition as claimed in claim 1 wherein the ratio of the oleic acid lower alkyl ester (b) to the fatty acid (a) is about 50:50 vol./vol.

6. A composition as claimed in claim 1 wherein the fatty acid is propionic acid.

7. A composition as claimed in claim 1 comprising 25% wt./vol. of the carbamate acetylcholinesterase inhibiting compound.

8. A method for the transdermal deliver of a carbamate acetylcholinesterase inhibiting compound comprising applying to the skin of a patient in need of same a transdermal delivery vehicle comprising:

(a) a $C_2$ to $C_4$ fatty acid, (b) oleic acid or a $C_1$ to $C_4$ alkyl ester thereof in a ratio of (b) to (a) of 40:60 to 60:40 vol./vol., and (c) 10–15% wt./vol of a therapeutic and/or prophylactic agent comprising a carbamate acetylcholinesterase inhibiting compound.

9. A method as claimed in claim 8 wherein the carbamate acetylcholinesterase inhibiting compound is physostigmine.

10. A method as claimed in claim 8 wherein component (b) is ethyl oleate.

11. A method as claimed in claim 8 wherein the ratio of the oleic acid or its ester to the fatty acid is from 45:55 to 55:45 vol./vol.

12. A method as claimed in claim 11 wherein the ratio of the oleic acid or its ester to the fatty acid is about 50:50 vol./vol.

13. A method as claimed in claim 8 wherein the fatty acid is propionic acid.

14. A transdermal delivery device comprising the composition of claim 1.

15. A transdermal delivery tape or patch comprising the composition of claim 1.

* * * * *